United States Patent
Zhang

(10) Patent No.: US 8,828,271 B2
(45) Date of Patent: Sep. 9, 2014

(54) HOT MELT WETNESS INDICATOR ADHESIVE COMPOSITION CONTAINING UV FLUORESCENT AGENT

(75) Inventor: Chongyao Zhang, Shorewood, WI (US)

(73) Assignee: Bostik, Inc., Wauwatosa, WI (US)

( * ) Notice: Subject to any disclaimer, the term of this patent is extended or adjusted under 35 U.S.C. 154(b) by 358 days.

(21) Appl. No.: 12/496,803

(22) Filed: Jul. 2, 2009

(65) Prior Publication Data

US 2010/0264369 A1 Oct. 21, 2010

Related U.S. Application Data

(60) Provisional application No. 61/078,067, filed on Jul. 3, 2008.

(51) Int. Cl.
*A61L 15/56* (2006.01)
*A61L 15/58* (2006.01)

(52) U.S. Cl.
CPC .............. *A61L 15/56* (2013.01); *A61L 15/58* (2013.01); *Y10S 252/963* (2013.01); *Y10S 252/964* (2013.01)
USPC ...... 252/301.35; 252/963; 252/964; 524/271; 524/272; 524/275; 524/322; 524/718

(58) Field of Classification Search
USPC ............. 252/301.35, 963, 964; 524/271, 272, 524/275, 322, 718
See application file for complete search history.

(56) References Cited

U.S. PATENT DOCUMENTS

| | | | |
|---|---|---|---|
| 4,231,370 A | 11/1980 | Mroz et al. | |
| 4,681,576 A | 7/1987 | Colon et al. | |
| 4,743,238 A | 5/1988 | Colon et al. | |
| 4,895,567 A | 1/1990 | Colon et al. | |
| 5,035,691 A | 7/1991 | Zimmel et al. | |
| 5,342,861 A * | 8/1994 | Raykovitz | 523/111 |
| 5,851,611 A * | 12/1998 | Guttag | 428/35.7 |
| 6,772,708 B2 * | 8/2004 | Klofta et al. | 116/206 |
| 7,059,760 B2 * | 6/2006 | Mehta et al. | 366/138 |
| 2004/0172000 A1 | 9/2004 | Roe et al. | |
| 2007/0264420 A1 * | 11/2007 | Davies et al. | 427/8 |
| 2010/0004613 A1 * | 1/2010 | Cohen | 604/361 |

FOREIGN PATENT DOCUMENTS

WO  02/36177 A2  5/2002
WO  WO 02/36177  *  5/2002

OTHER PUBLICATIONS

International Search Report/Written Opinion, PCT International Application No. PCT/US2009/049479, mailed Aug. 4, 2010.

\* cited by examiner

*Primary Examiner* — Carol M Koslow
(74) *Attorney, Agent, or Firm* — Wozny Law, LLC; Thomas M. Wozny

(57) ABSTRACT

A wetness indicating adhesive composition comprising an adhesive base composition incorporating a fluorescing agent in the adhesive base composition that only fluoresces when wet, and not when dry. In one embodiment, the adhesive base composition may be composed of water soluble, or at least partially water soluble, components, and in another embodiment the adhesive base composition may be composed of water sensitive components as for example one or more water insoluble polymers and a surfactant. The fluorescing agent can either be dissolved or dispersed in the adhesive base composition, and is preferably a water soluble fluorescing agent that becomes visible under ultraviolet light only when an article such as a disposable diaper becomes wet.

31 Claims, No Drawings

HOT MELT WETNESS INDICATOR ADHESIVE COMPOSITION CONTAINING UV FLUORESCENT AGENT

FIELD OF THE INVENTION

The invention relates to a hot melt wetness indicator adhesive composition that can be used in disposable nonwoven absorbent articles. The indicator adhesive will indicate wetness when body fluid is discharged from the wearer by fluorescing when exposed to an Ultraviolet light. This allows the article to be checked for wetness even in a dark environment by using a UV light.

BACKGROUND OF THE INVENTION

Disposable nonwoven absorbent products have widespread acceptance for infant, young child and incontinent adult care applications. Typical disposable nonwoven absorbent articles include diapers, training pants, adult incontinent pads and briefs, feminine sanitary napkins or pads and tampons. Disposable nonwoven absorbent articles such as those mentioned function to receive and contain urine and other body fluids that the wearer secretes. These items are worn against or in close proximity to the skin of the wearer.

Typical disposable nonwoven absorbent articles consist of a fluid—impervious film back sheet, a porous fluid permeable nonwoven top sheet and an absorbent core sandwiched between the top and back sheets. These articles are usually bonded using hot melt adhesives. In addition to this basic construction, these absorbent articles usually have many other features to either improve the body fluid containment function or to enhance the comfort level for the wearer. For example, infant diapers contain elastic leg cuffs attached to the top sheet for enhanced fluid containment.

Since disposable nonwoven absorbent articles are widely used for body fluid containment function, it is desirable to know whether the article is wet and thus requires replacement. Monitoring of wetness by visual inspection can be time consuming and unpleasant. It is therefore invaluable to incorporate a function to signal wetness into a disposable nonwoven absorbent article such as a diaper.

Approaches using coating stripes of wetness indicator adhesives, or wetness indicators to signal wetness by way of color change have been described in Mroz et al., U.S. Pat. No. 4,231,370. This article discloses an improved absorbent product having a wetness indicator disposed between a translucent cover member and an absorbent member. According to the disclosure, the wetness indictor is applied in the form of a stripe to a portion of the inwardly facing surface of a back sheet of a disposable diaper. Such a wetness indictor contains a pH—change/color—change type of colorant dispersed in a water-based adhesive latexes of styrene/2-ethylhexylacrylate copolymer, ethylene/vinyl acetate copolymer, or polyvinyl acetate. The indicator adheres to the back sheet and dries to a flexible coating that is yellow in color. When insulted by body secretions such as urine, the indicator changes from yellow to blue, signaling the presence of moisture. To obtain a suitable pH, sufficient acid buffering means such as phosphoric acid must be added to the latexes. Phosphoric acid is a harsh acid, which could raise safety concerns. Another disadvantage of the Mroz et al latex-based composition and any similar water or solvent-based products is that the means of water or solvent removal has to be provided during manufacturing.

Colon et al. U.S. Pat. Nos. 4,681,576, 4,743,238 and 4,895,567 disclose hot melt wetness indicator adhesives that change color upon insult with urine or water. These adhesives are based on a water-soluble polyvinyl pyrrolidone polymer, or a water soluble vinyl pyrrolidone—vinyl acetate copolymer, or an ethylene-acrylic acid copolymer in combination with a fatty acid and a wetness indicating dye. The composition can contain a variety of other ingredients such as water-soluble waxes, glycerol esters, ethylene—vinyl acetate copolymers and hydrogenated oils, etc.

Zimmel et al., U.S. Pat. No. 5,035,691 discloses a hot melt wetness indicator composition based on an adduct which is prepared by reacting ethylene-acrylic acid copolymer with polyethylene oxide under monobutyl tin (IV) oxide catalyst. The composition contains 0.03 to 0.5 wt % acid-base indicator as the active ingredient to signal the presence of moisture.

Raykovitz, U.S. Pat. No. 5,342,861 discloses a composition similar to that of Zimmel et al. in that the composition comprises a wetness indicating agent such as a pH indicator, a graft copolymer prepared by reacting a vinyl polymer with low molecular weight polyethylene oxide and a compatible tackifier.

The prior art compositions herein mentioned above have several deficiencies. The hot melt wetness indicator composition disclosed in Colon et al, for example, exhibits poor thermal stability. Thus, when heated at elevated temperatures between 250-300° F., which is typically encountered during hot melt application, the adhesives can severely degrade as manifested by char, skin formulation and color darkening. Most of the components in Colon's composition are incompatible with each other, and therefore, the composition can suffer from phase separation during application at the typical hot melt adhesive coating conditions. Other deficiencies are the poor environmental stability and poor bleed-through or wash-out resistance that typical polyvinylpyrrolidone homo- or co-polymer based formulations suffer after the indicator is applied to a typical polymer film substrate. The coated indicator tends to change slowly and prematurely from yellow to green and finally to blue from exposure to atmospheric moisture during storage. This aspect is particularly important since finished nonwoven adsorbent products can be stored for a few months before they reach consumer's hands. A premature color change during storage will render the product useless. An additional deficiency is the poor intensity of color change of the indicator when insulted resulting in the color change being barely visible through translucent substrates. The compositions taught by Zimmel et al. and Raykovitz, on the other hand, necessitate harsh conditions to carry out chemical grafting of low molecular weight hydrophilic PEG to another relatively high molecular weight hydrophobic polymer. Their grafting reactions require either an organotin catalyst (Zimmel) or a peroxide initiator (Raykovitz). Problems can arise from product safety concerns with residual organotin compounds and peroxides. Since the hydrophilic PEG is typically incompatible with the vinyl polymer used for preparation of the graft copolymer, the unreacted reactants can pose compatibility problems for the final wetness indicator composition.

In view of the deficiencies of the prior art products, needs exist for a new wetness indicating adhesive composition that is compatible, that is thermally and environmentally stable, that has intense color change and good wash-out resistance, that can withstand multiple insults during use, and that is easy to manufacture and apply.

All of the prior art disclosures involve the use of various indicators that change color under visible light conditions either in response to changes in pH when contacted with a liquid such as urine or when contacted by a liquid per se. However, it would be advantageous to be able to check for wetness in a dark environment, for example while the wearer is sleeping, without having to wake the person. The present invention discloses the use of wetness indicating adhesive compositions containing a fluorescing agent that does not fluoresce when dry, but instead is activated and becomes visible to the human eye in the dark and/or under a UV light only when the article becomes wet. This feature is not disclosed or suggested in any of the prior art listed.

SUMMARY OF THE INVENTION

The present invention is directed towards a wetness indicating adhesive composition comprising an adhesive base composition incorporating a fluorescing agent in the adhesive base composition that only fluoresces when wet, and not when dry. In one embodiment, the adhesive base composition may be composed of water soluble, or at least partially water soluble, components, and in another embodiment the adhesive base composition may be composed of water sensitive components as for example one or more water insoluble polymers and a surfactant. The fluorescing agent can either be dissolved or dispersed in the adhesive base composition, and is preferably a water soluble fluorescing agent.

Preferably the adhesive is a hot melt adhesive. Hot melt adhesives are preferred over other types of adhesives for many reasons. Unlike water-based or solvent-based adhesives, there is no liquid carrier that needs to be evaporated. Hot melts are applied in a molten state and solidify when cooled. Thus they can be applied at much faster line speeds since no drying needs to occur. Hot melts also tend to stay in place better since they stop flowing as soon as they cool. This is important when trying to extrude or print a pattern of adhesive. However, it is conceivable for some applications that the adhesive base composition can be a water-based adhesive rather than a hot melt adhesive provided the requisite compatible fluorescing agent is incorporated into the water-based adhesive composition.

The fluorescing agent that is blended into the adhesive base composition is not visible when dry, but is visible only when the adhesive becomes wet, and as a result, either becomes visible to the human eye in the dark or becomes visible under exposure to light, such as infrared light, visible light (red, orange, yellow, green, blue, indigo or violet), or ultraviolet (UV) light. The preferred light is UV light, and the preferred fluorescing agents include, but are not limited to, Fluorescein (free acid) 2-(6-hydroxy-3-oxo-(3H)-xanthen-9-yl)benzoic acid distributed by Sigma-Aldrich, Fluorescein sodium salt (disodium 6-hydroxy-3-oxo-9-xanthene-o-benzoate) also from Sigma-Aldrich, and Pyranine 10G (8-hydroxy-1,3,6-pyrenetrisulfonic acid trisodium salt) from Keystone Aniline. The amount of fluorescent agents in the adhesive base composition may range from 0.001% to 5% by weight, preferably from 0.01% to 1% by weight, most preferably from 0.1% to 0.5% by weight. The fluorescing agent may be a single compound having fluorescent properties or may also comprise a blend of one or more individual fluorescing compounds.

In one embodiment, the wetness indicating adhesive composition is based on an at least partially water soluble hot melt adhesive base which includes a polymer that may be a homopolymer, copolymer, terpolymer, interpolymer or blends thereof together with a tackifying resin, a stabilizer, and the fluorescing agent included as the primary ingredients. Optionally, the wetness indicating adhesive composition may also include a conventional pH wetness indicator such as an acid-base wetness indictor agent that changes color in response to changes in pH when contacted by a liquid such as urine, or a dye that is capable of changing color when insulted with urine. The composition of the present invention has overcome the deficiencies of the prior art wetness indicators. One embodiment of the present invention is to provide a wetness indictor that has excellent heat and environmental stability, improved fastness, vivid color change, easy manufacturing, and easy application. Another embodiment is directed towards a composition that has a delayed response and therefore can withstand multiple insults daily.

The hot melt wetness indicator composition of the present invention can be applied using a variety of conventional coating techniques known in the art. It is especially suited for slot die, multibeads, spiral spray and different variations of melt-blown coatings.

The preferred wetness indicator adhesive composition of the present invention is a hot melt adhesive composition that comprises as ingredients thereof a mixture of the following components:

a. a polymer or blend of polymers in the amount of about 10% to 80% by weight, and preferably in the range of about 15-45% by weight;

b. a tackifier or blend of tackifiers in the amount of about 20% to 70% by weight, and preferably in the amount of about 35% to 65% by weight;

c. a surfactant or blend of surfactants in the amount of about 0% to 30% by weight, and preferably in the amount of about 0.1-15% by weight;

d. a plasticizer or blend of plasticizers in the amount of about 0-50% by weight, and preferably in the amount of about 5% to 40% by weight;

e. a wax or blend of waxes in the amount of about 0% to 50% by weight and preferably in the amount of about 5% to 40% by weight;

f. about 0-5% by weight of one or more of a stabilizer or antioxidant;

g. a conventional wetness indicating agent such as a pH indicator or acid-base indicator in the amounts of about 0% to 5% by weight, and preferably in the amounts of 0.05% to 0.2% by weight; and h. a fluorescing agent in the amount of 0.001% to 5% by weight, preferably in the amount of 0.01% to 1% by weight, and most preferably from 0.1% to 0.5% by weight.

The components of the composition add up to 100% by weight. The adhesive may contain other conventional ingredients such as a filler or a colorant that can modify the color of the above basic adhesive composition.

DETAILED DESCRIPTION OF THE INVENTION

In accordance with the present invention, a hot melt wetness indicator is formulated, comprising about 10 to 80% by weight of a polymer component, about 20 to 70% by weight of a compatible tackifier, about 0 to 60% by weight of a surfactant, about 0 to 50% of a wax, about 0.001 to 5% by weight of a fluorescing agent, about 0 to 50% by weight of a plasticizer, and about 0 to 5% by weight of a stabilizer or antioxidant, and optionally about 0% to 5% by weight of a wetness indicating agent such as a pH indicator. Other optional ingredients can be added to modify or enhance the physical and performance characteristics of the composition. Such optional ingredients include, but are not limited to, a filler, an inert dye or colorant, a second polymer, etc.

Any of a variety of available thermoplastic materials can be used, either alone or as a blend, as the polymer ingredient in the compositions of the invention. With respect to the adhesive composition, the polymer may be a homopolymer, a copolymer, a terpolymer, an interpolymer, or blends thereof, and may be present in an amount from about 10% to about 80% by weight, preferably from about 15% to about 45%, and most preferably from about 20% to about 35%. Examples of such thermoplastic materials include ethylene based polymers, including ethylene/vinyl acetate (EVA), ethylene acrylate, ethylene methacrylate, ethylene methyl acrylate, ethylene methyl methacrylate, high and low density polyethylene, polyethylene blends and chemically modified polyethylene, copolymers of ethylene and 1-6 mono- or di-unsaturated monomers, ethylene/styrene interpolymers (ESI), polyesters such as sulfonated polyesters; amorphous polyalphaolefins (APAOs), including atactic polypropylene, and others; metallocene catalyzed polyalphaolefins; SIS (styrene-isoprene-styrene) block copolymer; SBS (styrene-butadiene-styrene) block copolymer; SEBS (styrene-ethylene-butylene-styrene) block copolymer; SEEPS (styrene-ethylene/ethylene-propylene styrene) block copolymer; SBR (styrene-butadiene-rubber); acrylic polymers and copolymers; as well as styrene acrylic polymers and copolymers; polybutene-1 homopolymers and copolymers, commonly referred to as polybutylene, linear A-B-A block, linear A-$(B-A)_n$-B multiblock copolymers, and radial or teleblock copolymers of the formula $(A-B)_n$-Y wherein A comprises a polystyrene block, B comprises a substantially rubbery polybutadiene or polyisoprene block, Y comprises a multivalent compound, and n is an integer of at least 3. The midblocks can be post-treated to improve their heat stability through hydrogenation or other post-treatment removing residual unsaturation. The size and the amount of the A or end blocks in the A-B-A block copolymer structure may be as much as 14-51 wt-% of the polymer.

In addition, water soluble polymers may also be employed as the thermoplastic material. Common water soluble polymers include polyesters such as sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, and polyvinylpyrrolidone/vinyl acetate. Other water soluble polymers may be used depending upon the desired end use and properties of the polymer, and thus the above list should neither be considered all-inclusive nor limiting on the scope of the term "thermoplastic material" or "thermoplastic polymer" as used herein.

Preferred thermoplastic polymers for use in the compositions of this invention are ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene-propylene-styrene (SEEPS) block copolymer, high density and low density polyethylene, polyethylene blends and chemically modified polyethylene, sulfonated polyesters, polyvinylpyrrolidone/vinyl acetate copolymer, amorphous polyalphaolefins especially atactic polypropylene (atactic PP), ethylene/styrene interpolymers (ESI), metallocene catalyzed APAOs, polyvinyl methyl ether, and polyethylene glycol polymers.

While the total styrene content of the polymers can be as much as 51 wt-% of the polymer, and since the polymers can have more than two A blocks for optimal performance, the total A block should be less than or equal to about 45 wt-% of the polymers, and, most preferably, is less than or equal to 35 wt-% of the polymer. In an S-B-S (styrene-butadiene-styrene) copolymer, the preferred molecular weight is about 50,000 to 120,000, and the preferred styrene content is about 20 to 45 wt-%. In an S-I-S (styrene-isoprene-styrene) copolymer, the preferred molecular weight is about 100,000 to 250,000 and the preferred styrene content is about 14-35 wt-%. Hydrogenating the butadiene midblocks produces rubbery midblocks that are typically considered to ethylene-butylene midblocks.

Such block copolymers are available from Kraton Polymers LLC, Enichem Elastomers Americas, Inc. and Dexco Polymers. Multiblock or tapered block copolymers (the A-$(B-A)n$-B type) are available from Firestone.

The tackifying resins which are used in the hot melt adhesives of the present invention are those which extend adhesive properties and improve specific adhesion. As used herein, the term "tackifying resin" includes:

a. natural and modified rosin such as, for example, gum rosin, wood rosin, tall-oil rosin, distilled rosin, hydrogenated rosin, dimerized rosin and polymerized rosin;

b. glycerol and pentaerythritol esters of natural and modified rosin, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall-oil rosin, and the phenolic modified pentaerythritol ester of rosin;

c. polyterpene resins having a softening point, as determined by ASTM method E28-58T, of from about 20° C. to 140° C., the latter polyterpene resins generally resulting from the polymerization of terpene hydrocarbons, such as the monoterpene known as pinene, in the presence of Friedel-Crafts catalysts at moderately low temperatures; also included are the hydrogenated polyterpene resins;

d. copolymers and terpolymers of natural terpenes, e.g. styrene/terpene, α-methyl styrene/terpene and vinyl toluene/terpene;

e. phenolic-modified terpene resins such as, for example, the resin product resulting from the condensation, in an acidic medium, of a terpene and a phenol;

f. oligomeric amide ester resin such as, for example, Unirez 2620 from Arizona Chemical;

g. aliphatic petroleum hydrocarbon resins having Ring and Ball softening points of from about 10° C. to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Cray Valley US;

h. aromatic petroleum hydrocarbons and the hydrogenated derivatives thereof;

i. aliphatic/aromatic petroleum derived hydrocarbons and the hydrogenated derivatives thereof.

Mixtures of two or more of the above described tackifying resins may be required for some formulations. Although a range of 20-70% by weight tackifying resin may be used, the preferred range is 35% to 60% and the most preferred range is 45% to 60%. An example of a commercially available tackifying resin which is useful for the present invention includes the resin which is identified commercially by the trade designation Sylvalite RE 100L. This resin is a pentaerythritol based tall-oil rosin ester, and Sylvalite RE 85L, a glycerol ester of tall oil rosin, both are available from Arizona Chemical Company.

Commercially available polymerized and modified rosins may be secured from Arizona Chemical Company under the trade designations "Sylvaros PR R, PR R85, and Uni-Tac 70," respectively. Commercially suitable partially hydrogenated rosins may be available from Eastman Chemical Company under the trade designations "Foral AX" and "Stabelite."

The wetness indicator composition of the present invention contains from about 0 to 30% by weight, and preferably about 0.1% to 15% by weight, and most preferably about 2% to about 10% by weight, of a surfactant to make the adhesive more hydrophilic and to impart water permeability to the composition. The surfactants suitable for use herein comprise cationic, anionic or nonionic types with the nonionic type preferred. The more preferred surfactant is selected from a group of nonionic surfactants having HLB less than 15. These surfactants include alkyl amines and amides; alkanolamines and amides; amine oxides; ethoxylated fatty alcohols, ethoxylated fatty acids, ethoxylated alkylphenols, ethoxylated amines or amides; ethoxylated fatty esters and oils; glycerol fatty esters and their ethoxylated derivatives; sorbitan derivatives; sucrose and glucose esters and their derivatives. The most preferred surfactants will have a HLB between 3 and 12 and are selected from a subgroup including ethoxylated fatty alcohols, ethoxylated fatty acids, stearic acid, glycerol esters of fatty acids and their derivatives and sorbitan derivatives. Mixtures of two or more surfactants herein described above may be used for some formulations.

As used herein, the term "surfactant" or "surface-active agent" refers to any compound that reduces surface tension when dissolved in water or water solutions, or which reduces interfacial tension between two liquids, or between a liquid and a solid. Examples of suitable surfactants include, but are not limited to, the following:

1. Fatty acid esters such as glycerol esters, PEG esters, and sorbitan esters, including ethylene glycol distearate, ethylene glycol monostearate, glycerol mono and/or dioleate, PEG dioleate, PEG monolaurate, sorbitan monolaurate, sorbitan trioleate, etc. These surfactants are available from ICI, Rhone-Poulenc, and other sources.
2. Nonionic ethoxylates such as alkylphenol ethoxylates, alcohol ethoxylates, alkylamine ethoxylates, etc., including octylphenol ethoxylate, nonylphenol ethoxylate, alkylamine ethoxylates, etc. These surfactants are available from Rhone-Poulene, Union Carbide, and other sources.
3. Nonionic surfactants such as 2,4,7,9-tetramethyl-5-decyn-4,7-diol available from Air Products.
4. Ethylene oxide/Propylene oxide copolymers which are available from Union Carbide, BASF, etc. It should be noted that these and other surfactants can be blended if necessary to produce the best blend of hydrophilic performance properties.

Atmer 129, a glycerol monostearate, manufactured by Uniquema Corporation, Atmer 688, a nonionic surfactant blend manufactured by ICI Americas, Inc., and Aerosol OT 100% surfactant (dioctyl sodium sulfosuccinate) made by Cytec Industries, Inc. have been found to be preferred surfactants for use in the present adhesive composition.

Both water soluble and water insoluble plasticizers can be present in the composition of the present invention either alone or in any desired combination in amounts of about 0% to about 50% by weight, preferably from about 5% to about 40% by weight, and most preferably from about 20% to about 35% by weight, in order to provide desired viscosity control without substantially decreasing the adhesive strength or the service temperature of the adhesive. Both liquid and solid plasticizers can be used in the composition of the present invention.

The water soluble plasticizers used herein comprise low molecular weight polyethylene glycols, multifunctional alcohol and the general class of surfactants wherein the molecules contain both a hydrophilic group and a hydrophobic group. The hydrophilic group of the molecule generally consists of, but is not limited to, polyethylene glycol, polypropylene glycol, a mono- or di-hydroxylated amino group, an ethoxylated amino radical, polyalkylene glycol esters of carboxylic group, substituted or unsubstituted glycerol, glucose, sucrose and sorbitan groups. The hydrophobic group of the molecule generally consists of, but is not limited to, a hydrocarbon radical such as, alkylphenol groups, dialkyl phenol groups, or a linear or branched aliphatic radicals. The preferred soluble plasticizers include ethoxylated alkyphenols, ethoxylated fatty acids and ethoxylated fatty alcohol having a HLB value in the range of 8.0-20.0. An ethoxylated alkyphenol with HLB value of 13.5 can be obtained under the trade designation Triton X-100 from Union Carbide Corporation of Danbury, Conn., and water soluble ethoxylated fatty acids, such as polyethylene glycol 600 monolaurate (HLB=14.6) and polyethylene glycol 1000 dilaurate (HLB=14.2), can be purchased from Stepan Company of Northfield, Ill. under the trade designations of Kessco PEG 600MC and PEG 1000DL, respectively.

A suitable water insoluble plasticizer may be selected from the group which includes dipropylene glycol dibenzoate, pentaerythritol tetrabenzoate; polyethylene glycol 400-di-2-ethylhexoate; 2-ethylhexyl diphenyl phosphate; butyl benzyl phthalate, dibutyl phthalate, dioctyl phthalate, various substituted citrates, and glycerates. Suitable dipropylene glycol dibenzoate and pentaerythritol tetrabenzoate may be purchased from Velsicol Chemical Company of Chicago, Ill. under the trade designations "Benzoflex 9-88 and S-552", respectively. Further, a suitable polyethylene glycol 400-di-2-ethylhexoate may be purchased from C.P. Hall Company of Chicago, Ill. under the trade designation "Tegmer 809". A suitable 2-ethylhexyl diphenyl phosphate, and a butyl benzyl phthalate may be purchased from Monsanto Industrial Chemical Company of St. Louis, Mo. under the trade designation "Santicizer 141 and 160", respectively.

A suitable plasticizer may be selected from the group which not only includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animal oils include glycerol esters of the usual fatty acids and polymerization products thereof. The plasticizer that finds usefulness in the present invention can be any number of different plasticizers but the inventors have discovered that mineral oil such as Kaydol manufactured by Sonneborn, Inc., is particularly useful in the present invention. Benzoflex 9-88, a dipropylene glycol dibenzoate, and Benzoflex 352, 1,4-cyclohexanedimethanol dibenzoate, both manufactured by Velsicol, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications).

As an optional ingredient to signal the presence of moisture, as for example when insulted with urine, a sufficient amount of wetness indicating agent may be used in the composition of the present invention. Useful wetness indicating agents include dyestuffs or colorants and pH indicators which are capable of changing the color of the adhesive composition when insulted with urine or water. Acid-base indicators, which change color in response to a change in pH are preferred and those having a color change at a pH of about 2-7 are more preferred. This pH is one created by the interaction between moisture and the hot melt composition set forth above. Such a pH is created in the hot melt indicator as moisture permeates the hydrophilic organic matrix. The most preferred acid-base indicators include bromophenol blue, bromo chlorophenol blue, bromocresol green and bromocresol purple. Typically they are present in the amounts of about 0.01 to 5% by weight and the amounts of about 0.05% to 0.2% by weight is more preferred. The acid-base indicators herein above described can be purchased from Aldrich Chemical Company Inc. of Milwaukee, Wis.

The wetness indicating agent produces a visual signal perceptible to the human eye under visible light to indicate that the absorbent article has been wetted. For example, the visual signal may be a change in color, such as from a first color to a second color, from one shade of a color to a different shade of the color, from a light or translucent color to a darker color, etc. The wetness indicating agent is used in an amount effective to provide the composition with a readily visible color when wet that is distinguishable from the color of the dry composition.

It is preferred that the wetness indicating agent is an acid-base wetness indicator that changes color in response to changes in pH when contacted by a liquid, such as urine. Suitable conventional acid-base wetness indicating agents include, for example, known wetness indicating agents such as those described in U.S. Pat. No. 5,066,711 to Colon et al. and U.S. Pat. No. 6,904,865 to Klofta et al., which are hereby incorporated by reference. For example, the conventional acid-base wetness indicating agent may comprise a sulfonepthalein pH indicator, such as Ethyl Red, Bromophenol Blue, Bomocresol Green, M-cresol Purple, Cresol Red, Cholorophenol Red, Bromothymol Blue, Bromopyrogallol red, Bromoxylenol Blue, and Bromophenol Blue; monoazo dye, such as acid alizarin violet N; monoazo pyrazoline dye, such as acid yellow 34; diazo dye, such as acid black 24; amphoteric anthraquinone dye, such as acid black 48; amphoteric anthraquinone dye, such as acid blue 45; triphenylmethane dye, such as acid fuchsin; phthalein type dye, such as o-cresolphtalein; xanthene dye, such as 2',7'-dicholorofluorescein eosin B; heterocylic acridine aromatics, such as acridine orange; dipehylmethane dye, such as auromine O; triphenylmethane dye, such as basic fuchsin; cationic thiazine dye, such as azure C; cationic anthraquinone dye, such as basic blue 47; phthalocyanine type dye, such as copper phthalocyanine; quaternized phthalocyanine type dye, such as alcec blue; cationic polymethine dye, such as astrzon orange G; anthraquinone type dye, such as alizarin; neutral complex dye, such as azure A eosinate; terpene type dyes, such as trans-beta-carotene; and the like.

The wetness indicating agent may also be an indicator that changes color when contacted by a liquid. Suitable conventional wetness indicating agents that change color when contacted by or dissolved in a liquid include, for example, known wetness indicating agents such as those described in U.S. Pat. No. 3,675,654 to Baker et al. and U.S. Pat. No. 5,342,861 to Raykovitz, which are hereby incorporated by reference. For example, the conventional wetness indicating agent may comprise a water soluble dye, such as a nitro dye, monoazo dye, diazo dye, phthalocyanine dye, quinoline dye, xanthene dye, triaryl methane dye, indigoid dye, vegetable dye, food dye, and the like.

The present invention may include a stabilizer in an amount of from about 0% to about 5% by weight. Preferably from about 0.1% to 1% of a stabilizer is incorporated into the composition. The stabilizers which are useful in the hot melt wetness indicator adhesive compositions of the present invention are incorporated to help protect the polymers noted above, and thereby the total adhesive system, from the effects of thermal and oxidative degradation which normally occurs during the manufacture and application of the indicator as well as in the ordinary exposure of the final product to the ambient environment. Among the applicable stabilizers are high molecular weight hindered phenols and multifunction phenols, such as sulfur and phosphorous-containing phenols. Hindered phenols are well known to those skilled in the art and may be characterized as phenolic compounds that also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl)benzene;

pentaerythritol tetrakis-3(3,5-di-tert-butyl-4-hydroxyphenyl) propionate;

n-octadecyl-3(3,5-di-tert-butyl-4-hydroxyphenyl) propionate;

4,4'-methylenebis(4-methyl-6-tert butylphenol);

2,6-di-tert-butylphenol;

6-(4-hydroxyphenoxy)-2,4-bis(n-octylthio)-1,3,5-triazine;

2,3,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-3(3,5-di-tet-butyl-4-hydroxy-phenyl) propionate.

Especially preferred as a stabilizer is pentaerythritol tetrakis-3(3,5-di-tert-butyl-4-hydroxyphenol) propionate.

The performance of these stabilizers may be further enhanced by utilizing, in conjunction therewith; (1) synergists such as, for example, thiodipropionate esters and phosphites; and (2) chelating agents and metal deactivators such as, for example, ethylenediamenetetraacetic acid, salts thereof, and disalicylalpropylenediimine.

It should be understood that other optional additives may be incorporated into the adhesive composition of the present invention in order to modify particular physical properties. These may include, for example, such materials as inert colorants, e.g., titanium dioxide, and fillers. Typical fillers include talc, calcium carbonate, clay silica, mica, wollastonite, feldspar, aluminum silicate, alumina, hydrated alumina, glass microspheres, ceramic microspheres, thermoplastic microspheres, baryte and wood flour.

The hot melt adhesive composition of the present invention may be formulated using any of the techniques known in the art. A representative example of the prior art mixing procedure involves placing all the components, except the polymer, fluorescing agent and the wetness indicator, in a jacketed mixing kettle equipped with a rotor, and thereafter raising the temperature of the mixture to a range from 250 to 300° F. to melt the contents. It should be understood that the precise temperature to be used in this step would depend on the melting points of the particular ingredients. The polymers are subsequently introduced to the kettle under agitation and the mixing is allowed to continue until a consistent and uniform mixture is formed. Finally, the wetness indicator and fluorescing agent are added and mixing is terminated when the wetness indicator and fluorescing agent become completely dissolved in the mixture. The contents of the kettle are protected with inert gas such as carbon dioxide and nitrogen during the entire mixing process.

The resulting hot melt wetness indicator may then be applied to substrates using a variety of coating techniques. Examples include hot melt slot die coating, hot melt wheel coating, hot melt roller coating, melt-blown coating and spiral spray coating. In a preferred embodiment, the hot melt adhesive is coated onto a substrate using slot-die having 1-5 mm wide nozzles to produce a coated pattern having multiple wetness indicator stripes on the back sheet.

The adhesive composition of the present invention may be used in a number of nonwoven absorbent articles applications such as, for example, in disposable nonwoven infant and young child diapers, training pants, adult incontinent pads and briefs, etc.

The wetness indicating adhesive composition includes a fluorescing agent that fluoresces only when wet, and not when dry. By the term "wet" or "wetted" it is meant that the adhesive comes into contact with a water-based fluid such as urine, saline solution, blood, mucous and other bodily exudates, as well as water itself. The fluorescing agent is used in an amount effective to provide the composition with a fluorescence, which can easily be seen in the dark to indicate that the absorbent article has been wetted.

The fluorescing agent may produce a fluorescence that is visible to the human eye in the dark and/or under visible light. However, it is preferred that the fluorescing agent is a fluorescent wetness indicating agent which produces a fluorescence that is visible to the human eye when exposed to light, such as infrared light, visible light (red, orange, yellow, green, blue, indigo, or violet), or ultraviolet (UV) light. Preferably, UV light from a UV light source (e.g., a black light) is used in combination with a UV activatable fluorescent wetness indicating agent.

The fluorescing agent is preferably water soluble such that is activated to produce a fluorescence in response to contact with a liquid. For example, the fluorescing agent is inactive when the adhesive composition is dry. When the adhesive composition containing the fluorescing agent is contacted with or dissolved in a liquid, and the fluorescing agent is activated, it produces a fluorescence when irradiated by light, preferably UV light. The fluorescing agent is preferably contained in a hot-melt adhesive so that it is only activated upon exposure to an aqueous environment. It should be noted that by varying the amount of fluorescing agent in the composition (typically increasing the amount), or by utilizing an appropriately sensitive fluorescing agent, there may be enough UV light emitted from conventional incandescent and/or fluorescent bulbs to cause the agent to fluoresce.

Suitable fluorescing agents include, for example, known compounds having fluorescent properties such as those disclosed in U.S. Pat. No. 3,941,759 to Taylor et al., U.S. Pat. No. 4,841,156 to May et al., U.S. Pat. No. 5,667,840 to Tingey et al., U.S. Pat. No. 6,080,450 to Canor, U.S. Pat. No. 6,391,281 to Rueggeberg et al., and U.S. Pat. No. 6,461,326 to Yang et al., which are hereby incorporated by reference. For example, the fluorescing wetness indicating agent may comprise an acridine dye, such as Acridine Orange and Acridine Yellow; cyanine dye, such as Cy3 and Cy5; xanthene dye, such as Eosin, Fluorescein, and Thodamine; pyrene dye, such as Alex Fluor® and AMCA-X; benzoxazole dye, such as Uvitex® OB; fluoranthene dye; quinine dye; and the like. Preferably, the fluorescing agent is a water soluble fluorescing agent, such as Fluorescein, 2-(6-hydroxy-3-oxo-(3H)-xanthen-9-yl)benzoic acid, or Fluorescein sodium salt (disodium 6-hydroxy-3-oxo-9-xanthene-o-benzoate) from Sigma-Aldrich, and Pyranine 10G (8-hydroxy-1,3,6-pyrenetrisulfonic acid trisodium salt) from Keystone Aniline.

Tests and Materials

Viscosity was tested according to ASTM D-3236 Method at 250° F. Ring & Ball softening point was determined with an automated Herzog unit according to ASTM E-28 Method.

Compatibility was determined by observing the phase behavior of the molten adhesive composition. To carry out the test, about 50 grams of molten indicator sample was poured into a 4 oz glass jar. The jar containing the sample was then placed in an air-circulating oven at 250° F. The contents of the jar were inspected after 3 days. Phase separation manifested itself by the presence of two distinct layers. The sample was defined as compatible (C) if there was no phase separation, and otherwise it was defined as incompatible (IN).

The hot melt wetness indicator was coated between polyethylene film and tissue with appropriate adhesive coating weight. The specimen was then insulted with saline solution (Sensitive Eyes® from Bausch & Lomb, Inc.), the color change rate of the wetness indicator was observed and reported within 60 seconds after the laminate was wetted by saline.

The UV light or black light used herein to test the fluorescent feature of wetness indicator was Koehler Bright Star model #1191 personal fluorescent UV light handset from China.

EXAMPLES

Several commonly used fluorescent agents were blended into a hot melt wetness indicator adhesive H9133-07, the mixes were coated between polyethylene film and tissue with a coating weight 22 grams/square meter, the laminates were then tested using commercially available saline from Bausch & Lomb, and the results are listed in Table 1.

TABLE 1

| Mixes | Uvitex OB | Coumarin | Trans-stilbene | Quinine | Fluorescein (free acid) | Fluorescein Sodium salt | Pyranine 10G | Fluorescent under UV light | | |
|---|---|---|---|---|---|---|---|---|---|---|
| | | | | | | | | Dry | Wet | Contrast |
| H9133-07 | 0.02% | | | | | | | Yes | Yes | No |
| Same | | 0.2% | | | | | | Yes | Yes | No |
| Same | | | 0.5% | | | | | Yes | Yes | No |

TABLE 1-continued

| Mixes | Uvitex OB | Coumarin | Trans-stilbene | Quinine | Fluorescein (free acid) | Fluorescein Sodium salt | Pyranine 10G | Fluorescent under UV light | | |
|---|---|---|---|---|---|---|---|---|---|---|
| | | | | | | | | Dry | Wet | Contrast |
| Same | | | | 0.2% | | | | Yes | Yes | No |
| Same | | | | | 0.2% | | | No | Yes | Yes |
| same | | | | | | 0.2% | | No | Yes | Yes |
| same | | | | | | | 0.2% | No | Yes | Yes |

H9133-07 is a commercial available hot melt wetness indicator from Bostik Inc.
Uvitex OB: 2,2'-(2,5-Thiophenediyl) bis[5-tert-butylbenzoxazole] from Ciba Specialty Chemicals
Coumarin: 7-diethylamino-4-methylcoumarin from Sigma-Aldrich
Trans-stilbene: trans-1,2-diphenylethene from Sigma-Aldrich
Quinine: (8-alpha, 9R)-6'-methoxycinchonan-9-ol from Sigma-Aldrich
Fluorescein (free acid): 2-(6-hydroxy-3-oxo-(3H)-xanthen-9-yl) benzoic acid distributed by Sigma-Aldrich
Fluorescein sodium salt: disodium 6-hydroxy-3-oxo-9-xanthene-o-benzoate from Sigma-Aldrich
Pyranine 10G: 8-hydroxy-1,3,6-pyrenetrisulfonic acid trisodium salt from Keystone Aniline Tables 2 and 3 list wetness indicators that can indicate whether articles are wet under both normal and UV lights

TABLE 2

Wetness indicators under normal light

| H9133-07 (contains pH indicator) | Initial color | Final color (after wetting by saline) | Color change rate (after wetting by Saline) |
|---|---|---|---|
| With 0.2% Fluorescein (free acid) | Yellow | Green | Instant color change |
| With 0.2% Fluorescein sodium salt | Yellow | Green | Instant color change |
| With 0.2% Pyranine 10G | Yellow | Green-blue | Instant color change |

TABLE 3

Wetness indicator under UV light

| H9133-07 | Initial color | Final color (after wetting by saline) | Color change rate (after wetting by saline) |
|---|---|---|---|
| With 0.2% Fluorescein free acid | Yellow | Bright fluorescence with yellow hue | Instant color change |
| With 0.2% Fluorescein sodium salt | Yellow | Bright fluorescence with yellow hue | Instant color change |
| With 0.2% Pyranine 10G | Yellow | Bright fluorescence with green hue | Instant color change |

Pyranine 10G can make SIS, SBS, SEBS, SEEPS, EVA, and APAO based hydrophilic hot melt adhesives glow under a UV light when the glue is wet. In order to make an adhesive being hydrophilic, 5% of Glycerol Monostearate is blended in each adhesive listed in Table 4 below except H20069 that is a hydrophilic SIS based hot melt.

Table 4 presents Pyranine 10G containing hydrophilic hot melt adhesives that fluoresce under UV light after wetting by saline solution.

TABLE 4

| Adhesives | Initial color | Final color under UV light |
|---|---|---|
| H20069 | None | Bright green fluorescence |
| H4244 | None | Bright green fluorescence |
| AFX-085A | None | Bright green fluorescence |
| H6040 | None | Bright green fluorescence |
| H1750 | None | Bright green fluorescence |
| H3257 | None | Bright green fluorescence |

H20069 is a hydrophilic SIS based hot melt adhesive available from Bostik Inc.
H4244 is a SBS based hot melt adhesive available from Bostik Inc.
AFX-085A is a SEBS based hot melt adhesive available from Bostik Inc.
H6040 is a SEEPS based hot melt adhesive available from Bostik Inc.
H1750 is an EVA based hot melt adhesive available from Bostik Inc.
H3257 is an APAO based hot melt adhesive available from Bostik Inc.

Several grades of water soluble polymers such as polyethylene glycols, sulfonated polyesters, and polyvinylpyrrolidone/vinyl acetate copolymers were used to make partially water-soluble or water sensitive hot melt adhesives with either Fluorescein free acid, Fluorescein sodium salt, or Pyranine 10G added thereto.

Tables 5 to 7 list hot melt adhesive examples that are fluorescent under UV light after wet by Saline solution.

TABLE 5

| Ingredients | Ex. 1 | Ex. 2 | Ex. 3 | Ex. 4 | Ex. 5 | Ex. 6 | Ex. 7 |
|---|---|---|---|---|---|---|---|
| Benzoflex 9-88 | 8 | 8 | | | | 10 | 10 |
| Benzoflex 352 | | | 13 | 5 | 5 | | |
| Century 1224 | 20 | 20 | | | | | |
| Atmer 129 | | | | | | 10 | 10 |
| Unirez 2620 | | | | | | 14.3 | 14.3 |
| Polyglykol 20000S | 28 | 36 | 28 | | | | |
| Polyglykol 8000S | | | | 29.8 | 33.8 | | |
| Foral AX | | | | | | 40 | 20 |
| Sylvaros TP 2040 | 43.3 | 35.3 | 58.3 | | | | |
| Sylvalite RE 85L | | | | | | | 20 |
| Sylvalite RE 100L | | | | 5 | 5 | | |
| Luvitec VA 64 | | | | | | 25 | 25 |
| AQ 2150 | | | | 59 | 55 | | |
| Irganox 1010 | 0.5 | 0.5 | 0.5 | 1 | 1 | 0.5 | 0.5 |
| Fluorescein free acid | 0.2 | 0.2 | 0.2 | 0.2 | 0.2 | 0.2 | 0.2 |

TABLE 6

| Ingredients | Ex. 8 | Ex. 9 | Ex. 10 | Ex. 11 | Ex. 12 | Ex. 13 | Ex. 14 |
|---|---|---|---|---|---|---|---|
| Benzoflex 9-88 | 8 | 8 | | | | 10 | 10 |
| Benzoflex 352 | | | 13 | 5 | 5 | | |
| Century 1224 | 20 | 20 | | | | | |
| Atmer 129 | | | | | | 10 | 10 |
| Unirez 2620 | | | | | | 14.3 | 14.3 |
| Polyglykol 20000S | 28 | 36 | 28 | | | | |
| Polyglykol 8000S | | | | 29.8 | 33.8 | | |
| Foral AX | | | | | | 40 | 20 |
| Sylvaros TP 2040 | 43.3 | 35.3 | 58.3 | | | | |
| Sylvalite RE 85L | | | | | | | 20 |
| Sylvalite RE 100L | | | | 5 | 5 | | |
| Luvitec VA 64 | | | | | | 25 | 25 |
| AQ 2150 | | | | 59 | 55 | | |
| Irganox 1010 | 0.5 | 0.5 | 0.5 | 1 | 1 | 0.5 | 0.5 |
| Fluorescein sodium salt | 0.2 | 0.2 | 0.2 | 0.2 | 0.2 | 0.2 | 0.2 |

TABLE 7

| Ingredients | Ex. 15 | Ex. 16 | Ex. 17 | Ex. 18 | Ex. 19 | Ex. 20 | Ex21 |
|---|---|---|---|---|---|---|---|
| Benzoflex 9-88 | 8 | 8 | | | | 10 | 10 |
| Benzoflex 352 | | | 13 | 5 | 5 | | |
| Century 1224 | 20 | 20 | | | | | |
| Atmer 129 | | | | | | 10 | 10 |
| Unirez 2620 | | | | | | 14.3 | 14.3 |
| Polyglykol 20000S | 28 | 36 | 28 | | | | |
| Polyglykol 8000S | | | | 29.8 | 33.8 | | |
| Foral AX | | | | | | 40 | 20 |
| Sylvaros TP 2040 | 43.3 | 35.3 | 58.3 | | | | |
| Sylvalite RE 85L | | | | | | | 20 |
| Sylvalite RE 100L | | | | 5 | 5 | | |
| Luvitec VA 64 | | | | | | 25 | 25 |
| AQ 2150 | | | | 59 | 55 | | |
| Irganox 1010 | 0.5 | 0.5 | 0.5 | 1 | 1 | 0.5 | 0.5 |
| Pyranine 10G | 0.2 | 0.2 | 0.2 | 0.2 | 0.2 | 0.2 | 0.2 |

Benzoflex 9-88: dipropylene glycol dibenzoate from Velsicol Chemical Corp.
Benzoflex 352: 1,4-cyclohexanedimethanol dibenzoate from Velsicol Chemical Corp.
Century 1224: octadecanoic acid from Arizona Chemicals
Atmer 129: glycerol monostearate from Ciba Specialty Chemicals
Uni-rez 2620: oligomeric amide ester resin from Arizona Chemicals
Polyglykol 20000S: polyethylene Glycol from Clariant Corp.
Polyglykol 8000S: polyethylene Glycol from Clariant Corp.
Foral AX: hydrogenated wood rosin from Eastman Chemicals
Sylvalite RE 85L: glycerol ester of tall oil rosin from Arizona Chemicals
Sylvalite RE 100L: pentaerythritol ester of tall oil rosin from Arizona Chemicals
Sylvares TP 2040: terpene phenol resin from Arizona Chemicals
Uvitec VA 64: polyvinylpyrrolidone/vinyl acetate copolymer from BASF Corp.
AQ 1250: sulfonated polyester from Eastman Chemicals
Irganox 1010: hindered phenol antioxidant from Ciba Specialty Chemicals
Fluorescein (free acid): 2-(6-hydroxy-3-oxo-(3H)-xanthen-9-yl) benzoic acid distributed by Sigma-Aldrich
Fluorescein sodium salt: disodium 6-hydroxy-3-oxo-9-xanthene-o-benzoate from Sigma-Aldrich
Pyranine 10G: 8-hydroxy-1,3,6-pyrenetrisulfonic acid trisodium salt from Keystone Aniline Unlike Pyranine 10G, Fluorescein (free acid) is pH dependent in terms of its fluorescent behavior. Table 8 compares the time the fluorescent agent takes to become bright under UV light after wet by solution with different pH value

TABLE 8

| H9133-07 | PH 4 solution | PH 5 solution | Saline |
|---|---|---|---|
| With 0.2% Fluorescein | 10 minutes (weak brightness) | immediate | immediate |
| With 0.2% Pyranine 10G | Immediate | immediate | immediate |

The Saline solution is commercially available from Bausch & Lomb.

The pH of human urine ranges from 5.8 to 7.4 based on the disclosure of J. L. Hammone, et al TAPPI Int. Dissolving Pulps Conf. (Geneva) Proc.: 247-264 (Mar. 24-27, 1987). As a result, fluorescein's relatively slow and weak fluorescing reaction at pH 4 actually will not affect its indicating function in articles such as disposable diapers that are obviously intended for human applications.

We claim:

1. A hot melt wetness indicating adhesive composition comprising a blend of the following ingredients:
   a. a polymer or a blend of polymers in an amount of about 10% to 80% by weight;
   b. a tackifier or a blend of tackifiers in an amount of about 20% to 70% by weight;
   c. a surfactant or a blend of surfactants in an amount of about 0% to 30% by weight;
   d. a plasticizer or a blend of plasticizers in an amount of about 0 to 50% by weight;
   e. a wax or a blend of waxes in an amount of about 0% to 50% by weight;
   f. about 0 to 5% by weight of a stabilizer or antioxidant;
   g. a wetness indicating agent or a blend of wetness indicating agents in an amount of about 0 to 5% by weight; and
   h. a fluorescing agent or a blend of fluorescing agents that fluoresce when exposed to infrared light, and only when wet and not when dry, in an amount of 0.001% to 10% by weight,
wherein the ingredients add up to 100% by weight of the composition.

2. The composition of claim 1 wherein said wetness indicating agent is selected from the group consisting of an acid-base indicator that changes color in response to changes in pH when contacted by a liquid, a dye that changes color in response to contact by a liquid, and blends thereof 3. The composition of claim 2 wherein said acid-base indicator is selected from the group consisting of a sulfonepthalein pH indicator, monoazo dye, monoazo pyrazoline dye, diazo dye, amphoteric anthraquinone dye, amphoteric anthraquinone dye, triphenylmethane dye, phthalein type dye, xanthene dye, heterocylic acridine aromatics, dipehylmethane dye, triphenylmethane dye, cationic thiazine dye, cationic anthraquinone dye, phthalocyanine type dye, quaternized phthalocyanine type dye, cationic polymethine dye, anthraquinone type dye, neutral complex dye, terpene type dyes, and blends thereof.

4. The composition of claim 2 wherein said dye is a water soluble dye selected from the group consisting of a nitro dye, monoazo dye, diazo dye, phthalocyanine dye, quinoline dye, xanthene dye, triaryl methane dye, indigoid dye, vegetable dye, food dye, and blends thereof.

5. The composition of claim 1 wherein said fluorescing agent is cyanine dye.

6. The composition of claim 1 wherein said fluorescing agent is water soluble.

7. The composition of claim 1 wherein said polymer is water soluble.

8. The composition of claim 1 wherein said polymer is selected from the group consisting of ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene-propylene-styrene (SEEPS) block copolymer, high density polyethylene, low density polyethylene, chemically modified polyethylene, sulfonated polyesters, polyvinylpyrrolidone/vinyl acetate copolymer, amorphous polyalphaolefins, ethylene/styrene interpolymers (ESI), metallocene catalyzed APAOs, polyvinyl methyl ether, and polyethylene glycol polymers.

9. The composition of claim 1 wherein the said tackifier is selected from the group consisting of natural rosin, modified rosin, polyterpene resins, copolymers of natural terpenes, terpolymers of natural terpenes, phenolic modified terpene resins, oligomeric amide ester resins, aliphatic petroleum hydrocarbon resins, aromatic petroleum hydrocarbon resins, and hydrogenated derivatives of said aromatic petroleum hydrocarbon resins.

10. The composition of claim 1 wherein the said surfactant is a nonionic surfactant, a cationic surfactant or an anionic surfactant.

11. The composition of claim 10 where the said nonionic surfactant is selected from the group consisting of alkyl amines and amides, alkanoamines and amides, amine oxides, ethoxylated fatty alcohols, ethoxylated fatty acids, ethoxylated alkylphenols, ethoxylated amines and amides, ethoxylated fatty esters and oils, glycerol fatty esters and their ethoxylated derivatives, sorbitan derivatives, sucrose esters and glucose esters and their derivatives.

12. The composition of claim 1 wherein the said plasticizer is a water soluble plasticizer.

13. The composition of claim 1 wherein the said plasticizer is a water insoluble plasticizer.

14. The composition of claim 1 wherein the said composition further includes a filler selected from the group consisting of talc, calcium carbonate, clay silica, mica, wollastonite, feldspar, aluminum silicate, alumina, hydrated alumina, glass microspheres, ceramic microspheres, thermoplastic microspheres, baryte, and wood flour.

15. A hot melt wetness indicating adhesive composition comprising a blend of the following ingredients:
 a. a polymer or a blend of polymers in an amount of about 10% to 80% by weight, said polymer or blend of polymers is water soluble;
 b. a tackifier or a blend of tackifiers in an amount of about 20% to 70% by weight;
 c. a surfactant or a blend of surfactants in an amount of about 0% to 30% by weight;
 d. a plasticizer or a blend of plasticizers in an amount of about 0 to 50% by weight;
 e. a wax or a blend of waxes in an amount of about 0% to 50% by weight;
 f. about 0 to 5% by weight of a stabilizer or antioxidant;
 g. a fluorescing agent or a blend of fluorescing agents that fluoresce when exposed to ultraviolet light, and only when wet and not when dry, in an amount of 0.001% to 10% by weight, said fluorescing agent or blend of fluorescing agents is water soluble; and
 h. a wetness indicating agent or blend of wetness indicating agents in an amount of about 0.01% to 5% by weight, wherein the ingredients add up to 100% by weight of the composition.

16. The composition of claim 15 wherein said wetness indicating agent is selected from the group consisting of an acid-base indicator that changes color in response to changes in pH when contacted by a liquid, a dye that changes color in response to contact by a liquid, and blends thereof.

17. The composition of claim 16 wherein said acid-base indicator is selected from the group consisting of a sulfonepthalein pH indicator, monoazo dye, monoazo pyrazoline dye, diazo dye, amphoteric anthraquinone dye, amphoteric anthraquinone dye, triphenylmethane dye, phthalein type dye, xanthene dye, heterocylic acridine aromatics, dipehylmethane dye, triphenylmethane dye, cationic thiazine dye, cationic anthraquinone dye, phthalocyanine type dye, quaternized phthalocyanine type dye, cationic polymethine dye, anthraquinone type dye, neutral complex dye, terpene type dyes, and blends thereof.

18. The composition of claim 16 wherein said dye is a water soluble dye selected from the group consisting of a nitro dye, monoazo dye, diazo dye, phthalocyanine dye, quinoline dye, xanthene dye, triaryl methane dye, indigoid dye, vegetable dye, food dye, and blends thereof.

19. The composition of claim 15 wherein said fluorescing agent is selected from the group consisting of an acridine dye, cyanine dye, xanthene dye, pyrene dye, benzoxazole dye, fluoranthene dye, quinine dye, and blends thereof.

20. The composition of claim 15 wherein said fluorescing agent is a sodium salt of fluorescein.

21. The composition of claim 15 wherein the said tackifier is selected from the group consisting of natural rosin, modified rosin, polyterpene resins, copolymers of natural terpenes, terpolymers of natural terpenes, phenolic modified terpene resins, oligomeric amide ester resins, aliphatic petroleum hydrocarbon resins, aromatic petroleum hydrocarbon resins, and hydrogenated derivatives of said aromatic petroleum hydrocarbon resins.

22. The composition of claim 15 wherein the said surfactant is a nonionic surfactant, a cationic surfactant or an anionic surfactant.

23. The composition of claim 22 where the said nonionic surfactant is selected from the group consisting of alkyl amines and amides, alkanoamines and amides, amine oxides, ethoxylated fatty alcohols, ethoxylated fatty acids, ethoxylated alkylphenols, ethoxylated amines and amides, ethoxylated fatty esters and oils, glycerol fatty esters and their ethoxylated derivatives, sorbitan derivatives, sucrose esters and glucose esters and their derivatives.

24. The composition of claim 15 wherein the said plasticizer is a water soluble plasticizer.

25. The composition of claim 15 wherein the said plasticizer is a water insoluble plasticizer.

26. The composition of claim 15 wherein the said composition further includes a filler selected from the group consisting of talc, calcium carbonate, clay silica, mica, wollastonite, feldspar, aluminum silicate, alumina, hydrated alumina, glass microspheres, ceramic microspheres, thermoplastic microspheres, baryte, and wood flour.

27. A hot melt wetness indicating adhesive composition comprising a blend of the following ingredients:
 a. a polymer or a blend of polymers in an amount of about 10% to 80% by weight, said polymer or blend of polymers is water soluble;
 b. a tackifier or a blend of tackifiers in an amount of about 20% to 70% by weight;

c. a surfactant or a blend of surfactants in an amount of about 0% to 30% by weight;
d. a plasticizer or a blend of plasticizers in an amount of about 0 to 50% by weight;
e. a wax or a blend of waxes in an amount of about 0% to 50% by weight;
f. about 0 to 5% by weight of a stabilizer or antioxidant;
g. a fluorescing agent or a blend of fluorescing agents that fluoresce when exposed to ultraviolet light, and only when wet and not when dry, in an amount of 0.001% to 10% by weight; and
h. a wetness indicating agent or blend of wetness indicating agents in an amount of about 0.01% to 5% by weight,
wherein the ingredients add up to 100% by weight of the composition.

28. A hot melt wetness indicating adhesive composition comprising a blend of the following ingredients:
a. a polymer or a blend of polymers in an amount of about 10% to 80% by weight, wherein said polymer is selected from the group consisting of ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene- propylene-styrene (SEEPS) block copolymer, high density polyethylene, low density polyethylene, chemically modified polyethylene, sulfonated polyesters, polyvinylpyrrolidone/vinyl acetate copolymer, amorphous polyalphaolefins, ethylene/styrene interpolymers (ESI), metallocene catalyzed APAOs, polyvinyl methyl ether, and polyethylene glycol polymers;
b. a tackifier or a blend of tackifiers in an amount of about 20% to 70% by weight;
c. a surfactant or a blend of surfactants in an amount of about 0% to 30% by weight;
d. a plasticizer or a blend of plasticizers in an amount of about 0 to 50% by weight;
e. a wax or a blend of waxes in an amount of about 0% to 50% by weight;
f. about 0 to 5% by weight of a stabilizer or antioxidant;
g. a fluorescing agent or a blend of fluorescing agents that fluoresce when exposed to ultraviolet light, and only when wet and not when dry, in an amount of 0.001% to 10% by weight; and
h. a wetness indicating agent or blend of wetness indicating agents in an amount of about 0.01% to 5% by weight,
wherein the ingredients add up to 100% by weight of the composition.

29. A hot melt wetness indicating adhesive composition comprising a blend of the following ingredients:
a. a polymer or a blend of polymers in an amount of about 10% to 80% by weight;
b. a tackifier or a blend of tackifiers in an amount of about 20% to 70% by weight;
c. a surfactant or a blend of surfactants in an amount of about 0% to 30% by weight;
d. a plasticizer or a blend of plasticizers in an amount of about 0 to 50% by weight;
e. a wax or a blend of waxes in an amount of about 0% to 50% by weight;
f. about 0 to 5% by weight of a stabilizer or antioxidant;
g. a fluorescing agent or blend of fluorescing agents that fluoresce when exposed to ultraviolet light, and only when wet and not when dry, in an amount of 0.001% to 10% by weight, said fluorescing agent is 8-hydroxy-1,3,6-pyrenetrisulfonic acid trisodium salt; and
h. a wetness indicating agent or blend of wetness indicating agents in an amount of about 0.01% to 5% by weight,
wherein the ingredients add up to 100% by weight of the composition.

30. A hot melt wetness indicating adhesive composition comprising a blend of the following ingredients:
a. a polymer or a blend of polymers in an amount of about 10% to 80% by weight;
b. a tackifier or a blend of tackifiers in an amount of about 20% to 70% by weight;
c. a surfactant or a blend of surfactants in an amount of about 0% to 30% by weight;
d. a plasticizer or a blend of plasticizers in an amount of about 0 to 50% by weight;
e. a wax or a blend of waxes in an amount of about 0% to 50% by weight;
f. about 0 to 5% by weight of a stabilizer or antioxidant;
g. a fluorescing agent or a blend of fluorescing agents that fluoresce when exposed to ultraviolet light, and only when wet and not when dry, in an amount of 0.001% to 10% by weight, said fluorescing agent or blend of fluorescing agents is water soluble, and wherein said fluorescing agent is fluorescein; and
h. a wetness indicating agent or blend of wetness indicating agents in an amount of about 0.01% to 5% by weight,
wherein the ingredients add up to 100% by weight of the composition.

31. A hot melt wetness indicating adhesive composition comprising a blend of the following ingredients:
a. a polymer or a blend of polymers in an amount of about 10% to 80% by weight, wherein said polymer is selected from the group consisting of ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene- propylene-styrene (SEEPS) block copolymer, high density polyethylene, low density polyethylene, chemically modified polyethylene, sulfonated polyesters, polyvinylpyrrolidone/vinyl acetate copolymer, amorphous polyalphaolefins, ethylene/styrene interpolymers (ESI), metallocene catalyzed APAOs, polyvinyl methyl ether, and polyethylene glycol polymers.
b. a tackifier or a blend of tackifiers in an amount of about 20% to 70% by weight;
c. a surfactant or a blend of surfactants in an amount of about 0% to 30% by weight;
d. a plasticizer or a blend of plasticizers in an amount of about 0 to 50% by weight;
e. a wax or a blend of waxes in an amount of about 0% to 50% by weight;
f. about 0 to 5% by weight of a stabilizer or antioxidant;
g. a fluorescing agent or a blend of fluorescing agents that fluoresce when exposed to ultraviolet light, and only when wet and not when dry, in an amount of 0.001% to 10% by weight, said fluorescing agent or blend of fluorescing agents is water soluble; and
h. a wetness indicating agent or blend of wetness indicating agents in an amount of about 0.01% to 5% by weight,
wherein the ingredients add up to 100% by weight of the composition.

* * * * *